United States Patent [19]

Hoehn et al.

[11] 4,127,715
[45] Nov. 28, 1978

[54] VARIOUS 1,5,10,11-TETRAHYDROBENZO[4,5]CYCLOHEPTA[1,2-B]PYRAZOLO-[4,3-E]PYRIDINE DERIVATIVES

[75] Inventors: Hans Hoehn, Tegernheim, Germany; Jack Bernstein, New Brunswick, N.J.; Berthold R. Vogt, Yardley, Pa.

[73] Assignee: E. R. Squibb & Sons, Inc., Princeton, N.J.

[21] Appl. No.: 881,470

[22] Filed: Feb. 27, 1978

Related U.S. Application Data

[62] Division of Ser. No. 781,619, Mar. 28, 1977, Pat. No. 4,087,433, which is a division of Ser. No. 698,992, Jun. 23, 1976, Pat. No. 4,033,970.

[51] Int. Cl.² ............................................ C07D 471/04
[52] U.S. Cl. ..................................................... 542/404
[58] Field of Search ...................... 542/404; 260/296 P

[56] References Cited

U.S. PATENT DOCUMENTS

| | | | |
|---|---|---|---|
| 4,018,779 | 4/1977 | Hoehn et al. ...................... 260/296 P |
| 4,033,970 | 7/1977 | Hoehn et al. ...................... 542/404 X |
| 4,062,858 | 12/1977 | Hoehn et al. ...................... 260/296 P |
| 4,087,433 | 5/1978 | Hoehn et al. ...................... 542/404 X |

*Primary Examiner*—John D. Randolph
*Attorney, Agent, or Firm*—Lawrence S. Levinson; Merle J. Smith; Stephen B. Davis

[57] ABSTRACT

Compounds of the formulas

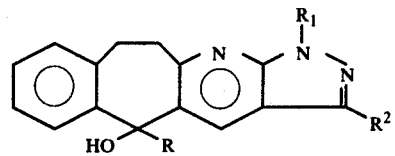

and

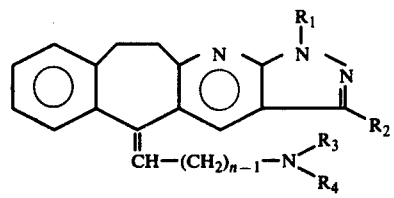

wherein $R_1$ is lower alkyl, phenyl, benzyl or phenethyl; $R_2$ is hydrogen, lower alkyl or phenyl;

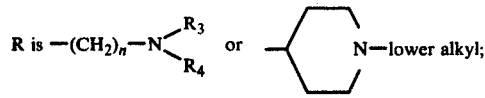

$n$ is an integer from 3 to 6; $R_3$ and $R_4$ are each lower alkyl or $R_3$ and $R_4$ taken together with the N-atom form a heterocyclic ring of the formula

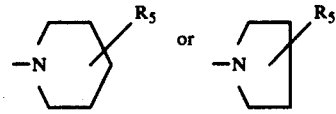

wherein $R_5$ is hydrogen, lower alkyl, or lower alkoxy; and pharmaceutically acceptable acid addition salts thereof are disclosed. These compounds and their salts possess central nervous system activity and are useful as anti-anxiety agents.

3 Claims, No Drawings

VARIOUS 1,5,10,11-TETRAHYDROBENZO[4,5]CYCLOHEPTA[1,2-B]PYRAZOLO-[4,3-E]PYRIDINE DERIVATIVES

This application is a division of Ser. No. 781,619 filed on Mar. 28, 1977 now U.S. Pat. No. 4,087,433 which in turn was a division of Ser. No. 698,992, filed June 23, 1976 and now U.S. Pat. No. 4,033,970.

SUMMARY OF THE INVENTION

This invention relates to new 1,5,10,11-tetrahydrobenzo[4.5]cyclohepta[1,2-b]pyrazolo[4,3-e]-pyridines and their acid addition salts of the formulas

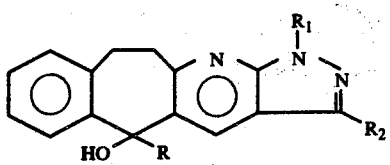

and

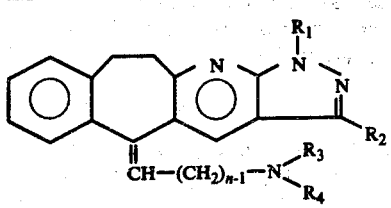

$R_1$ is lower alkyl, phenyl, benzyl, or phenethyl
$R_2$ is hydrogen, lower alkyl, or phenyl.
R is

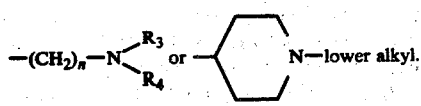

$n$ is an integer from 3 to 6.
$R_3$ and $R_4$ are the same or different and each is lower alkyl or $R_3$ and $R_4$ taken together with the N-atom form a heterocyclic of the formula

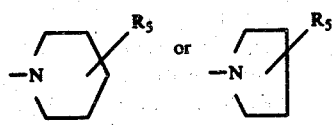

wherein $R_5$ is hydrogen, lower alkyl or lower alkoxy.

DETAILED DESCRIPTION OF THE INVENTION

The term "lower alkyl" as used throughout this specification is meant to include straight or branched chain hydrocarbon groups having from 1 to 4 carbon atoms, i.e., methyl, ethyl, n-propyl, i-propyl, n-butyl, i-butyl, and t-butyl. Similarly, the term "lower alkoxy" is meant to include such alkyl groups linked to an oxygen atom, i.e., methoxy, ethoxy, t-butoxy, etc.

Preferred embodiments of this invention are the compounds of formulas I and II wherein:
$R_1$ is lower alkyl of 1 to 4 carbons, especially ethyl.
$R_2$ is hydrogen.
R is

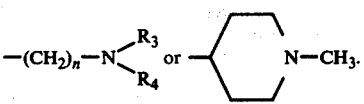

$n$ is 3.
$R_3$ and $R_4$ are the same and are methyl or ethyl, especially methyl.

The new compounds of formula I can be prepared by several methods. The preferred methods involve reacting a ketone of the formula

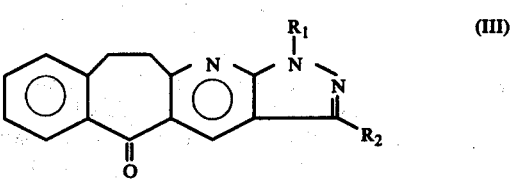

with a Grignard reagent of the formula

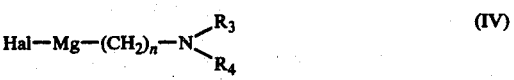

or

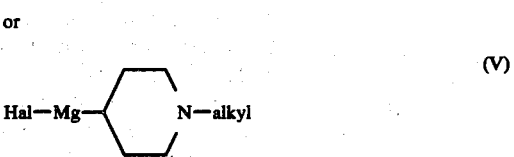

wherein Hal is Cl or Br and $n$, $R_1$, $R_2$, $R_3$ and $R_4$ are as defined above. This reaction is carried out in an inert solvent such as diethylether, dibutylether, or tetrahydrofuran by heating at about the reflux temperature for several hours.

Alternatively, certain compounds of formula I wherein $n$ is three can also be prepared by reacting the ketone of formula III with an alkyl magnesium halide Grignard reactant of the formula

to yield the compound of the formula

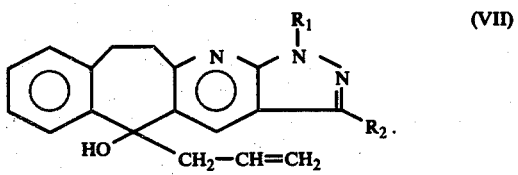

Amination of the olefinic linkage of the compound of formula VII by reacting with an amine

yields the compound of formula I wherein $n$ is 3.

Also, the ketone of formula III can be reacted with a dialkylaminoalkyne of the formula

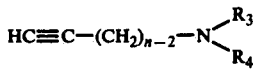
(VIII)

in the presence of a condensing agent such as sodium or lithium amide to yield the compound of the formula

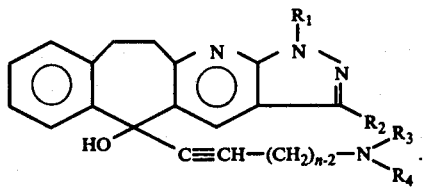
(IX)

Hydrogenation of the compound of formula IX yields the corresponding compound of formula I.

The new compounds of formula II are prepared by dehydrating the compound of formula I wherein R is

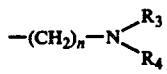

The dehydration is accomplished by heating the compound of formula I in an acid such as hydrochloric acid, polyphosphoric acid, etc., or a dehydrating agent such as acetic anhydride. The compounds of formula II are obtained as a mixture of the cis and trans isomers.

The preparation of the starting materials of formula III are disclosed in U.S. Ser. No. 670,332 filed on Mar. 25, 1976. As disclosed therein a 5-aminopyrazole of the formula

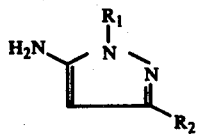
(X)

[prepared according to the procedure described in Z. f. Chemie 10, 386–388 (1970)] is reacted with a phenylpropionyl malonic acid dialkylester of the formula

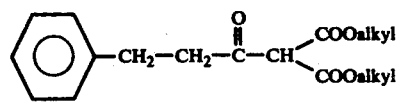
(XI)

[prepared according to the procedure described in J. Chromatography 47, 479 (1970)] by heating at a temperature of about 120° C in the presence of polyphosphoric acid, producing a compound of the formula

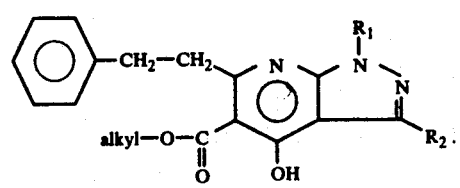
(XII)

The intermediate of formula XII is saponified by means of a basic agent like sodium hydroxide, etc., to yield an acid of the formula

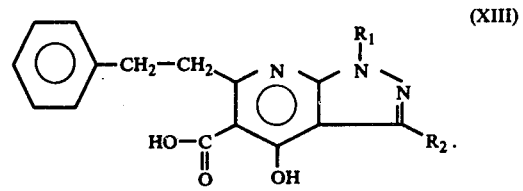
(XIII)

The compound of formula XIII is then cyclized by heating at a temperature of about 120° C using polyphosphoric acid as the ring closure agent, to produce a compound of the formula

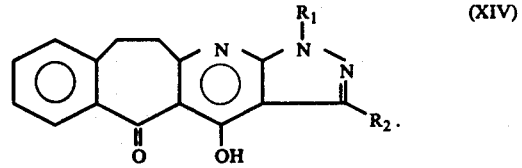
(XIV)

The tetracyclic heterocycle of the formula XIV is treated with an inorganic acid chloride or bromide such as phosphorous oxychloride, thionyl chloride, etc., to yield a compound of the formula

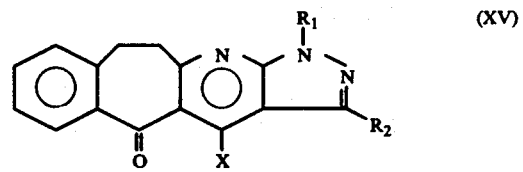
(XV)

wherein X is Cl or Br.

Treatment of the compound of the formula XV with triethylamine and hydrogenation with palladium on charcoal yields the starting material of formula III.

Depending on the reaction conditions and the starting materials used, the compounds of formulas I and II are obtained in the free form or in the form of their acid addition salts. The salts thereof can be converted into the free compounds in a known manner such as by reaction with a basic agent. Free bases which may be obtained can be converted into pharmaceutically acceptable acid addition salts by reaction with a variety of acids. Acids useful for preparing these acid-addition salts include, inter alia, inorganic acids, such as the hydrohalic acids (e.g. hydrochloric and hydrobromic acid), sulfuric acid, nitric acid, and phosphoric acid, and organic acids such as maleic, fumaric, tartaric, citric, acetic, benzoic, 2-acetoxybenzoic, salicylic, succinic, nicotinic, methanesulfonic or cyclohexanesulfamic.

The new compounds of formulas I and II including their acid addition salts are capable of modifying the central nervous system. When administered to mice, cats, rats, dogs, and other mammalian species in amounts ranging from about 0.5 mg. to about 100 mg. per kg. of body weight per day, these compounds in particular exhibit anti-anxiety activity. A preferred dosage regimen for optimum results would be from about 1 mg. to about 5 mg. per kg. of body weight per day, and such dosage units are employed so that a total of from about 35 mg. to about 3 g. of active ingredient in single or divided doses are administered in a 24 hour period.

Compounds of formula I when administered to rats within the above stated preferred dosage range produced a significant anti-anxiety effect as demonstrated by increases in behavior which were formerly suppressed by punishment in a conflict test procedure [cf. J. R. Vogel, B. Beer, D. Clody, Psychopharmacologist, 21, 1 (1970)].

For this pharmaceutical purpose a compound or mixture of compounds of formulas I and II or their pharmaceutically acceptable acid addition salts may be administered orally or parenterally in a conventional dosage form such as tablet, capsule, injectable or the like. These may be conventionally formulated in an oral or parenteral dosage form by compounding with a conventional vehicle, excipient, binder, preservative, stabilizer, flavor or the like as called for by accepted pharmaceutical practice.

The following examples are illustrative of the invention and represent preferred embodiments. Other modifications may be readily produced by suitable variations of the reactions. All temperatures are on the centigrade scale.

EXAMPLE 1

5-[3-(Dimethylamino)propyl]-1-ethyl-1,5,10,11-tetrahydrobenzo[4,5]cyclohepta[1,2-b]pyrazolo[4,3-e]pyridin-5-ol, hydrochloride (1:2)

(a) 1-Ethyl-4-hydroxy-6-(2-phenylethyl)-1H-pyrazolo[3,4-b]-pyridine-5-carboxylic acid, ethyl ester 43.6 g. of (3-phenylpropionyl)malonic acid, diethyl ester (0.15 mol.) are added to a stirred mixture of 16.5 g. of 5-amino-1-ethylpyrazole (0.15 mol.) and 220 g. of polyphosphoric acid. The mixture is heated to 120° (bath temperature) for 50 minutes. After the mixture has cooled to room temperature, 250 ml. of water are added in portions and stirring is continued for 20 minutes. The aqueous phosphoric acid solution is then decanted and the undissolved residue is treated with 200 ml. of water and aqueous ammonia (10%) to neutralize the mixture. The mixture is extracted with chloroform and the chloroform extract is washed twice with water, dried with $Na_2SO_4$ and evaporated to yield 39 g. of the oily product. Dissolution of the oil in about 250 ml. of ether and addition of ethereal hydrogen chloride yields 35 g. (62%) of 1-ethyl-4-hydroxy-6-(2-phenylethyl)1H-pyrazolo[3,4-b]pyridine-5-carboxylic acid, ethyl ester, hydrochloride, m.p. 153°–155° (ethanol/ethyl acetate 1:1).

(b) 1-Ethyl-4-hydroxy-6-(2-phenylethyl)-1H-pyrazolo[3,4-b]-pyridine-5-carboxylic acid 64 g. of 1-ethyl-4-hydroxy-6-(2-phenylethyl)-1H-pyrazolo[3,4-b]pyridine-5-carboxylic acid, ethyl ester, hydrochloride (0.17 mol.), dissolved in 800 ml. of aqueous sodium hydroxide (20%), are heated at 80°–85° (bath temperature) for 44 hours. The solution is treated with charcoal, filtered and then acidified with half-concentrated hydrochloric acid. The precipitated 1-ethyl-4-hydroxy-6-(2-phenylethyl)-1H-pyrazolo[3,4-b]pyridine-5-carboxylic acid is filtered off, washed with water and dried in a desiccator to give 46.5 g. (88%) of 1-ethyl-4-hydroxy-6-(2-phenylethyl)-1H-pyrazolo-[3,4-b]pyridine-5-carboxylic acid, m.p. 160°–161° (absolute ethanol).

(c) 1-Ethyl-10,11-dihydro-4-hydroxybenzo [4,5] cyclohepta-[1,2-b]pyrazolo[4,3-e]pyridin-5(1H)one 46.6 g. of 1-ethyl-4-hydroxy-6-(2-phenylethyl)-1H-pyrazolo[3,4-b]pyridine-5-carboxylic acid (0.15 mol.) and 300 g. of polyphosphoric acid are heated at 200°–220° (bath temperature) with stirring for 20 minutes. After the mixture has cooled to room temperature, 700 ml. of ice-water are added slowly with stirring. The stirring is continued until the compound becomes crystalline. The collected ketone is then dissolved in chloroform and the solution is washed with water, treated with charcoal and dried ($Na_2SO_4$). Evaporation of the solution yields 30.3 g. (69%) of 1-ethyl-10,11-dihydro-4-hydroxybenzo [4,5] cyclohepta [1,2-b] pyrazolo [4,3-e]-pyridin-5(1H)one, m.p. 154°–155° (hexane).

(d) 4-Chloro-1-ethyl-10,11-dihydrobenzo[4,5]cyclohepta[1,2-b]-pyrazolo[4,3-e]pyridin-5(1H)one 26.5 g. of 1-ethyl-10,11-dihydro-4-hydroxybenzo-[4,5]cyclohepta[1,2-b]pyrazolo[4,3-e]pyridin-5(1H)one (0.09 mol.) are refluxed in 350 ml. of phosphorus oxychloride for 5 hours. The excess phosphorous oxychloride is removed in vacuo and the residue is treated with water and extracted with ether. The ethereal solution is washed twice with water, dried ($Na_2SO_4$) and then evaporated to give 26 g. (93%) of 4-chloro-1-ethyl-10,11-dihydrobenzo [4,5] cyclohepta [1,2-b] pyrazolo-[4,3-e] pyridin-5(1H)one, m.p. 111°–113° (hexane/cyclohexane 2:1).

(e) 1-Ethyl-10,11-dihydrobenzo [4,5] cyclohepta [1,2-b] pyrazolo-[4,3-e]pyridin-5(1H)one To a solution of 23.3 g. of 4-chloro-1-ethyl-10,11-dihydrobenzo[4,5]cyclohepta[1,2-b]pyrazolo[4,3-e]pyridin-5(1H)one (0.075 mol.) in 450 ml. absolute ethanol are added 22.5 g. of triethylamine and 2 g. of palladium on charcoal (10%). The mixture is hydrogenated at room temperature. After the solution has absorbed the theoretical amount of hydrogen, the reaction is filtered and the alcohol is removed by distillation. The residue is treated with water and after stirring for 20 minutes the compound is extracted with ether. The ethereal solution is washed with water, dried with anhydrous sodium sulfate and evaporated yielding 18.2 g. (88%) of 1-ethyl-10,11-dihydrobenzo [4,5] cyclohepta [1,2-b]pyrazolo[4,3-e]-pyridin-5(1H)one, m.p. 88°–90° (hexane).

(f) 5-[3-(Dimethylamino)propyl]-1-ethyl-1,5,10,11-tetrahydrobenzo [4,5] cyclohepta [1,2-b] pyrazolo [4,3-e] pyridin-5-ol, hydrochloride(1:2)

40 g. (0.33 mol.) of freshly distilled and absolutely dry 3-dimethylaminopropyl)chloride are added slowly with stirring and gentle heating to 8.0 g. of magnesium turnings in 200 ml. of dry tetrahydrofuran. A crystal of iodine and a few drops of ethyl iodide are employed as initiator. After all of the 3-dimethylaminopropyl chloride is added, the reaction mixture is refluxed for 2 to 3 hours. This Grignard reagent is then added to a solution of 30.5 g. (0.11 mol.) of 1-ethyl-10,11-dihydrobenzo[4,5-]cyclohepta-[1,2-b]pyrazolo[4,3-e]pyridin-5(1H)-one in 200 ml. of dry tetrahydrofuran. The mixture is heated under reflux for 2 hours after which the solvent is evaporated and the residue decomposed with 100 ml. of ice-water and 180 ml. of ammonium chloride solution (20%). This mixture is extracted with ether and the ethereal extract is washed with water, dried with $Na_2SO_4$, and the solvent evaporated to yield 28.7 g.(72%) of oily 5-[3-(dimethylamino)propyl]-1-ethyl-1,5,10,11-tetrahydrobenzo [4,5] cyclohepta [1,2-b] pyrazolo-[4,3-e] pyridin-5-ol.

This oil is dissolved in 250 ml. of dry ether and 22 ml. of ethereal hydrochloric acid (256 g. HCl/l.) are added to yield 25 g. of crude hydrochloride salt; m.p. 100°-102°. A sample of this salt is recrystallized from ethyl acetate/ether (1:2) to yield 5-[3-(dimethylamino)-propyl]-1-ethyl-1,5,10,11-tetrahydrobenzo [4,5] cyclohepta [1,2-b] pyrazolo [4,3-e] pyridin-5-ol, hydrochloride (1:2); m.p. 101°-103° (dec.).

EXAMPLES 2-20

Following the procedure of example 1 but employing the substituted 5-aminopyrazole shown below in Col. I one obtains the 10,11-dihydrobenzo [4,5] cyclohepta [1,2-b]pyrazolo-[4,3-e]pyridin-5(1H)-one shown in Col. II. Reaction of the ketone of Col. II with the Grignard reactant shown in Col. III yields the final product shown in Col. IV.

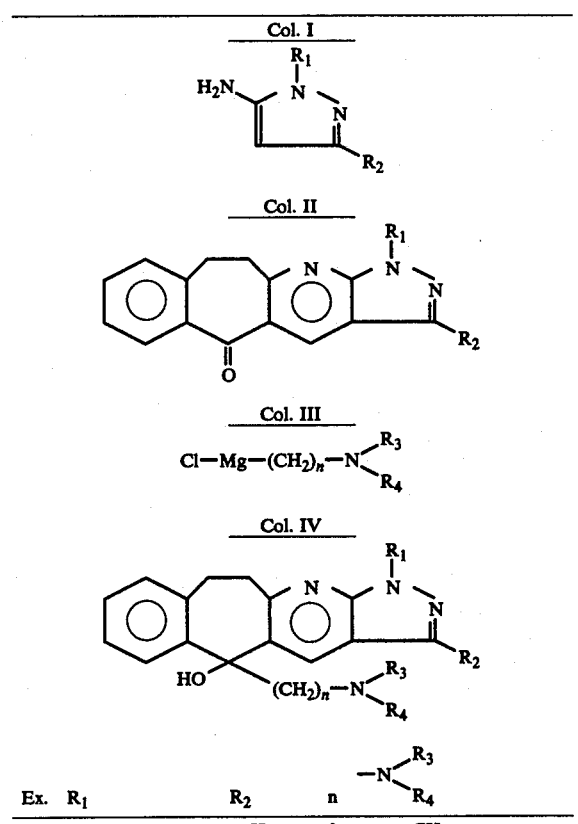

| Ex. | $R_1$ | $R_2$ | n | $-N\genfrac{}{}{0pt}{}{R_3}{R_4}$ |
|---|---|---|---|---|
| 2 | $-CH_3$ | $-H$ | 3 | $-N(CH_3)_2$ |
| 3 | $-i-C_3H_7$ | $-H$ | 4 | $-N(CH_3)_2$ |
| 4 | $-n-C_4H_9$ | $-H$ | 3 | $-N(C_2H_5)_2$ |
| 5 | $-t-C_4H_9$ | $-CH_3$ | 3 | $-N(CH_3)_2$ |
| 6 | $-H$ | $-H$ | 5 | $-N(CH_3)(C_2H_5)$ |
| 7 | $-C_6H_5$ | $-C_2H_5$ | 3 | $-N(CH_3)(C_3H_7)$ |
| 8 | $-CH_2-C_6H_5$ | $-H$ | 6 | $-N(CH_3)_2$ |
| 9 | $-(CH_2)_2-C_6H_5$ | $-H$ | 3 | $-N(C_2H_5)_2$ |
| 10 | $-C_2H_5$ | $-CH_3$ | 3 | $-N(CH_3)(t-C_4H_9)$ |
| 11 | $-C_2H_5$ | $-t-C_4H_9$ | 3 | $-N(CH_3)_2$ |
| 12 | $-C_2H_5$ | $-C_6H_5$ | 4 | $-N(C_2H_5)(C_3H_7)$ |
| 13 | $-C_2H_5$ | $-H$ | 3 | piperidinyl |
| 14 | $-CH_3$ | $-C_2H_5$ | 4 | 4-methylpiperidinyl |
| 15 | $-C_2H_5$ | $-H$ | 6 | 4-methoxypiperidinyl |
| 16 | $-C_2H_5$ | $-H$ | 3 | 4-ethoxypiperidinyl |
| 17 | $-C_2H_5$ | $-H$ | 3 | pyrrolidinyl |
| 18 | $-CH_2-C_6H_5$ | $-H$ | 4 | 2-ethylpyrrolidinyl |
| 19 | $-C_6H_5$ | $-C_2H_5$ | 3 | 3-methoxypyrrolidinyl |
| 20 | $-C_2H_5$ | $-CH_3$ | 5 | 4-methylpiperidinyl |

EXAMPLE 21

1-Ethyl-1,5,10,11-tetrahydro-5-(1-methyl-4-piperidinyl)-benzo [4,5] cyclohepta [1,2-b] pyrazolo [4,3-e] pyridin-5-ol, hydrochloride (1:2)

13.4 g. (0.1 mol.) of freshly distilled and absolutely dry 4-chloro-1-methylpiperidine and a few drops of ethyl iodide are added to 2.4 g. (0.1 mol.) of magnesium turnings. After all of the 4-chloro-1-methylpiperidine is added, the mixture is refluxed for 3 hours with stirring. After cooling, this Grignard reagent is added to a solution of 9.7 g. (0.035 mol.) of 1-ethyl-10,11-dihydro-benzo [4,5] cyclohepta [1,2-b] pyrazolo [4,3-e]-pyridin-5(1H)-one from example 1(e) in 75 ml. of dry tetrahydrofuran. While stirring, the mixture is refluxed for 3 hours. The solvent is then distilled off and the residue is treated successively with 50 ml. of ice-water and 100 ml. of a 20% aqueous ammonium chloride solution. This mixture is extracted with ether and the ethereal extract is washed with water, dried with $Na_2SO_4$, and the solvent is evaporated to yield 6.5 g. (49.5%) of 1-ethyl-1,5,10,11-tetrahydro-5-(1-methyl-4-piperidinyl)-benzo[4,5]-cyclohepta [1,2-b] pyrazolo [4,3-e] pyridin-5-ol; m.p. 189°–191° (cyclohexane).

This material is dissolved in ethyl acetate and ethereal hydrochloric acid is added to yield 1-ethyl-1,5,10,11-tetrahydro-5-(1-methyl-4-piperidinyl)benzo [4,5] cyclohepta-[1,2-b]pyrazolo [4,3-e] pyridin-5-ol, hydrochloride (1:2); m.p. 190°–191° (dec.).

EXAMPLES 22-27

Following the procedure of example 21 but employing the Grignard reactant shown below in Col. I one obtains the final products shown below in Col. II.

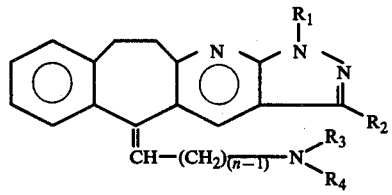

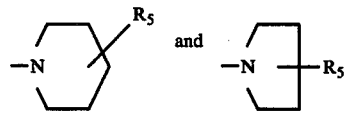

| Ex. | alkyl |
|---|---|
| 22 | —C$_2$H$_5$ |
| 23 | -n-C$_3$H$_7$ |
| 24 | -i-C$_3$H$_7$ |
| 25 | -n-C$_4$H$_9$ |
| 26 | -i-C$_4$H$_9$ |
| 27 | -t-C$_4$H$_9$ |

Similarly, by employing the 10,11-dihydrobenzo[4,5] cyclohepta [1,2-b] pyrazolo [4,3-e] pyridin-5(1H)-ones shown in Col. II of examples 2 to 20 within the procedure of examples 21-27, other compounds within the scope of the invention are obtained.

EXAMPLE 28

5-[3-(Dimethylamino)propylidene]-1-ethyl-1,5,10,11-tetrahydrobenzo[4,5]cyclohepta[1,2-b]pyrazolo[4,3-e]-pyridine, hydrochloride (1:2)

14.5 g. (0.033 mol.) of 5-[3-(dimethylamino)-propyl]-1-ethyl-1,5,10,11-tetrahydrobenzo [4,5] cyclohepta [1,2-b]pyrazolo[4,3-e]pyridine-5-ol, hydrochlorie (1:2) from example 1(f) are suspended in 125 ml. of acetic anhydride. After the addition of a few drops of pyridine, the mixture is heated at 55°–60° (bath temperature) for 14 hours with stirring. The resulting solution is filtered, evaporated, and the residual oily compound is extracted into ether. The ethereal extract is washed with an aqueous sodium bicarbonate solution and water (twice) and dried with anhydrous sodium sulfate. Removal of the ether leaves 11 g. of oily 5-[3-(dimethylamino)-propylidene]-1-ethyl-1,5,10,11-tetrahydrobenzo[4,5]cyclohepta[1,2-b]pyrazolo-[4,3-e]pyridine.

This oil is dissolved in 75 ml. of anhydrous ether and treated with ethereal hydrochloric acid while stirring to yield a crude hydrochloride salt. Recrystallization from a mixture of ethyl acetate and ether yields 5.2 g. (38%) of hygroscopic 5-[3-(dimethylamino)propylidene]-1-ethyl-1,5,10,11-tetrahydrobenzo[4,5]cyclohepta[1,2-b]-pyrazolo[4,3-e]pyridine, hydrochloride (1:2); m.p. 79°–81°.

Similarly, by employing the dehydration procedure of example 28 on the products shown in Col. IV of examples 2 to 20, other compounds within the scope of the invention are obtained.

What is claimed is:

1. A compound of the formula

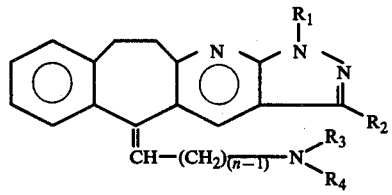

wherein R$_1$ is lower alkyl of 1 to 4 carbons, phenyl, benzyl, or phenethyl; R$_2$ is hydrogen, lower alkyl of 1 to 4 carbons, or phenyl; R$_3$ and R$_4$ taken together with the N-atom form a heterocyclic ring selected from the group consisting of

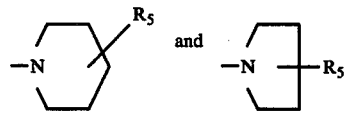

wherein R$_5$ is hydrogen, lower alkyl of 1 to 4 carbons, or lower alkoxy of 1 to 4 carbons; $n$ is an integer from 3 to 6; and a pharmaceuticaly acceptable acid addition salt thereof.

2. The compound of claim 1 wherein R$_1$ is lower alkyl of 1 to 4 carbons, R$_2$ is hydrogen, $n$ is 3 or 4, and R$_5$ is hydrogen, methyl or methoxy.

3. The compound of claim 2 wherein R$_1$ is ethyl and $n$ is 3.

* * * * *

UNITED STATES PATENT AND TRADEMARK OFFICE
CERTIFICATE OF CORRECTION

PATENT NO. : 4,127,715
DATED : November 28, 1978
INVENTOR(S) : Hans Hoehn et al.

It is certified that error appears in the above-identified patent and that said Letters Patent are hereby corrected as shown below:

Col. 9, line 51 should read :

--b]pyrazolo[4,3-e]pyridine-5-ol, hydrochloride (1:2) from --

Signed and Sealed this

Thirteenth Day of March 1979

[SEAL]

Attest:

RUTH C. MASON
Attesting Officer

DONALD W. BANNER
Commissioner of Patents and Trademarks